United States Patent
Hilal et al.

[11] Patent Number: 5,984,919
[45] Date of Patent: *Nov. 16, 1999

[54] SURGICAL TROCAR

[75] Inventors: Nabil Hilal, Mission Viejo; Said S. Hilal, Laguna Niguel, both of Calif.

[73] Assignee: Applied Medical Resources Corporation, Laguna Hills, Calif.

[*] Notice: This patent is subject to a terminal disclaimer.

[21] Appl. No.: 08/156,958

[22] Filed: Nov. 22, 1993

Related U.S. Application Data

[63] Continuation of application No. 07/654,815, Feb. 13, 1991, abandoned.

[51] Int. Cl.$^6$ ............................................. A61B 17/36
[52] U.S. Cl. ........................... 606/45; 606/41; 606/13; 604/264; 604/170
[58] Field of Search ............................ 606/37–42, 45–52, 606/167, 181–185; 604/164, 165, 170, 171, 264, 272

[56] References Cited

U.S. PATENT DOCUMENTS

| | | | |
|---|---|---|---|
| 1,741,461 | 12/1929 | Herman | 606/45 |
| 3,595,235 | 7/1971 | Petersen | 606/45 |
| 3,850,158 | 11/1974 | Elias et al. | 604/264 |
| 4,043,342 | 8/1977 | Morrison, Jr. | 606/48 |
| 4,418,692 | 12/1983 | Guay | 606/45 X |
| 4,750,489 | 6/1988 | Berkman et al. | 606/181 X |
| 4,800,878 | 1/1989 | Cartmell | 606/45 |
| 4,850,353 | 7/1989 | Stasz et al. | 606/45 |
| 4,869,248 | 9/1989 | Narula | 606/45 |
| 4,986,814 | 1/1991 | Burney et al. | 604/264 X |
| 5,009,656 | 4/1991 | Reimels | 606/48 |
| 5,057,099 | 10/1991 | Rink | 606/12 |
| 5,066,288 | 11/1991 | Deniega et al. | 606/134 |
| 5,071,222 | 12/1991 | Laakmann et al. | 606/28 X |
| 5,125,927 | 6/1992 | Belanger | 606/45 |
| 5,275,596 | 1/1994 | Long et al. | 606/27 X |

FOREIGN PATENT DOCUMENTS

WO 2488  8/1982  WIPO ................................ 606/45

*Primary Examiner*—Michael Peffley
*Attorney, Agent, or Firm*—Richard L. Myers

[57] ABSTRACT

A surgical trocar includes an operative sleeve adapted for disposition across a tissue barrier and an obturator removably disposed in the sleeve. A source of energy is introduced to a cutting element disposed at the distal end of the obturator for energizing the cutting element to cut tissue barrier. The distal end of the obturator and the distal end of the operative sleeve can be advanced through the cut tissue and the obturator removed leaving the sleeve operatively disposed for further surgery.

29 Claims, 5 Drawing Sheets

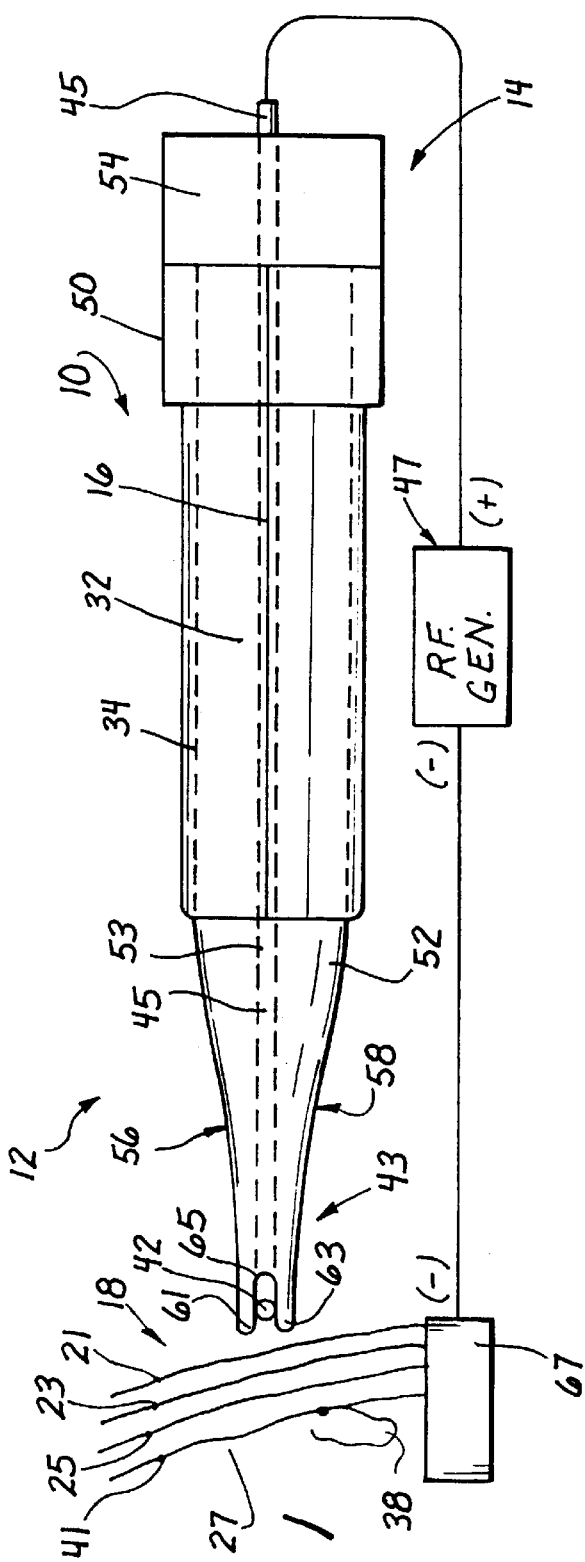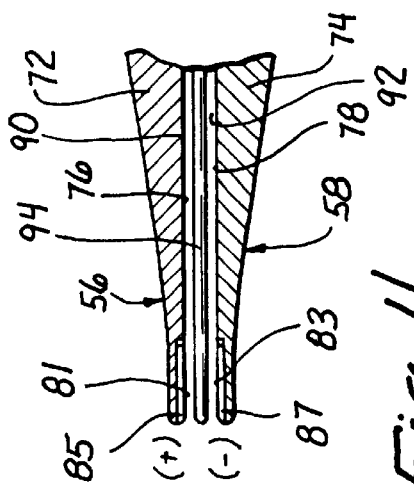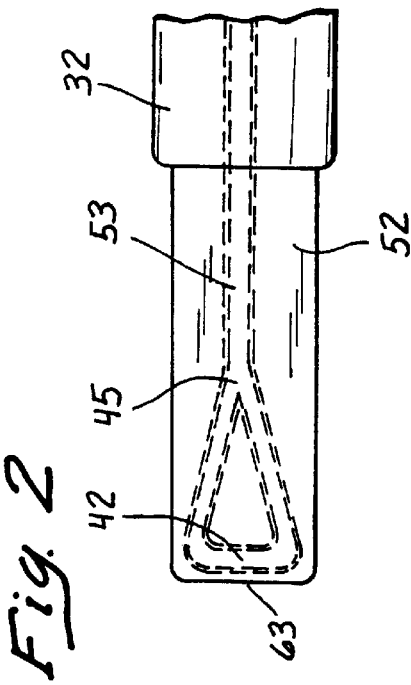

SURGICAL TROCAR

This application is a continuation of application Ser. No. 07/654,815, filed Feb. 13, 1991 now abandoned.

BACKGROUND OF THE INVENTION

Devices and procedures for providing an enlarged tubular access into a body cavity or body conduit, were first conceived when catheters became particularly valuable for noninvasive surgery. A catheter which may have had a diameter of such as 5 French is typically very flexible and therefore does not have the column strength necessary to puncture the skin or a vessel in order to accommodate insertion of the catheter. A method which is still the preferred procedure was developed whereby a common surgical needle is inserted through the skin and into the vessel. This needle was closely overlaid with a thin sheath, commonly referred to as an introducer, which is carried by the needle into the vessel. When the needle was removed, the introducer was left in place and provided the tubular access through which the catheter could then be inserted.

In more recent times, noninvasive surgery has further advanced so that large body cavities such as the abdomen can be accessed through tubular devices and the surgical procedures performed with long narrow instruments through those access devices. It is not surprising that these devices, commonly referred to as trocars, are introduced through the abdominal wall or other tissue barrier, in much the same manner as that employed by the catheter introducer systems. Thus, trocars typically include a puncturing device, commonly referred to as an obturator, and a closely spaced outer sheath or cannula. In this case the obturator may have an outside diameter such as 10 millimeters, where the cannula has a similar inside diameter. Once the cannula is in place, narrow surgical apparatus can be inserted through the cannula to perform common functions such as cutting, irrigating, aspirating, grinding, traction and removal of body parts.

While the above mentioned procedure for introducing catheters has remained satisfactory, this same procedure applied to trocars has not been effective for two primary reasons. First, the size of the required puncture is much larger than that associated with catheters. Second, the abdominal wall consists of a material having a much greater density than merely skin or vessel walls. The puncture required for a trocar must typically be made through muscle which provides a much higher resistance to entry. As a result of these two differences, forces as great as 100 pounds may be required to insert a trocar into a body cavity.

In order to accommodate forces of this magnitude, obturators have been formed from solid metal rods and provided with very sharp points and long cutting edges leading from the point to the outer circumference of the obturator. While this has had some effect on the force required for insertion, it has only aggravated the problem associated with the presence of organs in close proximity to the abdominal wall.

In order to avoid puncturing of these organs, it has been necessary to stop the forward movement of the trocar immediately upon penetration. Thus the procedure has called for a tremendous force in order to penetrate the abdominal muscle and an immediate stopping of that force at the point where there is no further resistance to forward movement. In some cases, physicians have attempted to avoid the significant forward pressure by twisting and turning the trocar. This has tended to significantly traumatize the incision.

More recently, attempts have been made to mechanically cover the sharp cutting tip and edges immediately following penetration. U.S. Pat. No. 4,654,030 discloses a sheath which is biased to move forwardly over the point of the trocar as soon as it penetrates the abdominal wall. Elaborate apparatus for biasing this sheath to the forward position have been complicated by requirements for a long throwing distance and a short throwing time.

The need has remained for an apparatus and method which can easily puncture (with a low force and providing a high degree of control) along a precise incision (providing low trauma and excellent healing characteristics) while avoiding any further cutting immediately following penetration.

SUMMARY OF THE INVENTION

These features are provided in accordance with the present invention which applies electrocautery techniques in the formation of a puncture wherein a long instrument, such as a trocar, can be advanced substantially perpendicular to the wall of a cavity, such as the abdominal wall. An electrocautery element such as a wire or blade can be provided at the distal end of the trocar and operated in accordance with monopolar or bipolar techniques to cut the abdominal wall as the trocar is advanced. Means can be provided for controlling the shape of the electrocautery element at the distal end of the trocar in order to vary the shape, for example the width, of the incision.

Apparatus for covering or retracting the electrocautery element immediately upon penetration of the wall is desirable to avoid cutting any proximate organs. This apparatus might include a pressure transducer responsive to the absence of pressure beyond the abdominal wall, or a logic circuit with properties for detecting a sharp reduction of cutting current upon penetration of the wall.

In one aspect of the invention, a surgical trocar assembly is provided for penetrating a barrier of tissue and providing an operative channel through the tissue barrier into a body cavity. The assembly includes an operative sleeve and an obturator removably disposed in the sleeve and extending beyond the distal end of the sleeve. A cutting element is disposed at the distal end of the obturator and adapted to be moved into contact with the tissue. Means is provided for conducting energy from a source to the cutting element and for energizing the cutting element to cut the tissue, whereby the distal end of the obturator and operative sleeve can be advanced through the cut tissue and across the tissue barrier.

In another aspect of the invention, a surgical apparatus is adapted for creating an incision through a tissue barrier. The apparatus includes a rod having walls disposed along a longitudinal axis and narrowing to form an apex at the distal end of the rod. Portions of the walls define a slot extending along a plane including the axis of the rod and means is disposed in the slot for conducting electrical energy toward the distal end of the rod. Means for energizing the conducting means facilitates cutting the tissue with the rod when the rod is placed in proximity to the tissue and when the rod is moved through the cut tissue to create the incision.

A method for inserting the cannula through the wall of a body cavity includes the steps of . . . inserting an energy conducting cutting device through the cannula; contacting the wall of the cavity with the cutting element; energizing the cutting element to cut the wall of the cavity; and advancing the tip of the cutting device to create an incision through the wall of the cavity.

These and other features and advantages associated with the present invention will be more apparent with a description of the preferred embodiments of the concept and reference to the associated drawings.

DESCRIPTION OF THE DRAWINGS

FIG. 1 is a side elevation view of one embodiment of the trocar associated with this invention operatively positioned to penetrate a tissue barrier;

FIG. 2 is a top plan view of the trocar embodiment illustrated in FIG. 1;

FIG. 4 is a cross-section view taken along lines 4—4 of FIG. 3.

DESCRIPTION OF PREFERRED EMBODIMENTS

Figure 3:
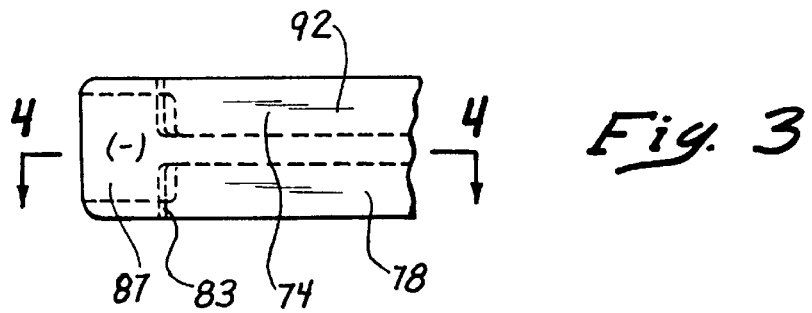
FIG. 3 is a top plan view of the distal end of a further embodiment of the trocar.

A surgical trocar is illustrated in FIG. 1 and designated generally by the reference numeral 10. The trocar 10 is a narrow elongate instrument having a distal end 12 and a proximal end 14. It is typically configured along a longitudinal axis 16 and is generally circular in radial cross-section.

It is the purpose of the trocar 10 to provide a channel through a tissue barrier in order to provide access across the barrier into a body cavity. By way of example, an abdominal wall 18 is illustrated in FIG. 1 and typically includes a layer of skin 21, a layer of fat 23, and a layer of muscle 25 which form the tissue barrier to an abdominal cavity 27.

The trocar 10 typically includes an elongate tube or cannula 32 having a cylindrical configuration and a wall thickness such as 0.015 inches. The cannula 32 has an interior bore or channel which is typically in a range of diameters between 5 to 12 millimeters. It is the purpose of the trocar 10 to pierce, cut, incise or otherwise puncture the tissue barrier, such as the abdominal wall 18, and to leave the cannula 32 extending through that incision with a channel 34 providing an access port into the cavity 27. Through this channel 34, various surgical instruments such as cutters, clamps, traction devices, visualization devices, aspirators and irrigators can be positioned and manipulated to perform a particular surgical procedure within the cavity 27.

The trocar 10 also includes an obturator 36 which extends through the cannula 32 and provides the means for cutting through the wall 18 to provide for insertion of the cannula 32. In the past, obturators have been formed from solid metal rods which have been sharpened to a point at the distal end 12 of the trocar 10. The forces necessary to puncture the abdominal wall 18 with such a device have been considerable due primarily to the presence of the muscle layer 25 in the wall 18. Puncturing of the wall 18 with such devices has been further complicated with the close proximity of important organs such as the liver 38 which, in some patients may actually be attached to the abdominal wall 18 by an adhesion 41. In order to avoid puncturing these organs, it has been an absolute requirement that the forward movement of the trocar 10 be stopped as soon as the distal tip of the obturator pierces through the interlayer of the wall 18. These conflicting requirements to provide a significant puncture force and then to immediately halt application of that force, have made the trocars of the past both difficult and dangerous to use.

In accordance with the present invention an obturator 36 includes a distal tip 43 which extends beyond the distal end of the cannula 32. This tip 43 is provided with at least one electrocautery wire 42 which can be activated through a conductor 45 by a radiofrequency generator 47.

Initially the trocar 10 is advanced until the wire 42 and the tip 43 are brought into contact with the tissue barrier such as the wall 18. Activating the wire 42 with radiofrequency energy causes the contacted cells to vaporize forming an opening or incision in the wall 18. With the application of a relatively minimal force, the trocar 10 can be advanced through the wall 18 until the tip 43 clears the inner layer of the wall 18, such as the muscle layer 25. At this point, it is desirable to de-energize the cutting element or wire 42 so that any further forward movement of the trocar 10 does not accidently cut an interior organ such as the liver 38. Various apparatus and methods for sensing this particular location and inhibiting further cutting are discussed in greater detail below.

At the proximal end 14 of the trocar 10 the cannula 32 is attached to a valving mechanism 50 which can be of the type disclosed by Moll in U. S. Pat. No. 4,654,030, or disclosed by applicant in copending U.S. patent application Ser. No. 07/630,078 filed on Dec. 19, 1990.

The obturator 36 includes an elongate shaft 52 which may include interior portions defining an axial channel 53 for the conductor 45. This shaft 52 extends through the valving mechanism 50 as well as the cannula 32 with the tip 43 extending beyond the distal end of the cannula 32. A finger knob 54 can be attached to the shaft 52 of the obturator 36 to facilitate application of the minimal axial force required to advance the trocar 10. Upon penetration of the wall 18, this finger knob 54 can be withdrawn proximally through the cannula 32 and the valving mechanism 50. In this manner, the cannula 32 is left in place with the interior channel 34 providing access across the abdominal wall 18 into the body cavity 27.

In the illustrated embodiment, the distal tip 43 of the obturator 36 has the configuration of a duck bill. It is defined primarily by a pair of opposing ramps 56, 58 which extend from the outer surface of the shaft 52 inwardly with progressive distal positions along the ramps 56, 68. At the distal end of the obturator 36, the ramps 56 and 58 terminate in a pair of lips 61, 63 respectively which define an interior recess 65 that is configured to receive the wire 42.

It will be noted that the lips 61, 63 extend slightly distally of the wire 42 by a particular distance. As the trocar 10 is moved forwardly, these lips 61, 63 are the only part of the trocar 10 which actually touch the wall 18. This particular distance is carefully selected, however, so that when the lips 61, 63 touch the wall 18, the wire 42 is close enough to the wall 18 that the most proximate cells vaporize to create the desired incision. This cutting by close proximity is commonly referred to as arcing. As used herein the cutting element, such as the wire 42, is deemed to be in contact with the wall 18 if the desired arcing or cutting occurs.

In the embodiment of FIG. 1, the electrocautery technique is monopolar; that is, only a single pole, such as the positive pole, is carried by the trocar 10. In this type of technique, the patient is laid directly on a large plate 67 which provides the second pole required by the electrocautery system. The RF generator 47 produces a radio frequency electrical energy signal which travels through the positive electrode connected to the wire 42 and through the body of the patient, to the negative pole at the plate 67. Where this conduction path is large in cross-section, the current density is very small. However, in proximity to the wire 42 the current path is very small in cross-section so the current density is quite large. It is this large current density which results in vaporizing the cells of the wall 18 in proximity to the wire 42.

It will be apparent that a bipolar electrocautery technique is equally applicable to this invention and may actually be preferred in some circumstances. A bipolar embodiment is illustrated in FIGS. 3 and 4 wherein the shaft 52 of the obturator 36 is separated axially into two half-shafts 72 and 74 each having in axial cross-section the shape of a half circle and each including one of the duck bills associated with the tip 43. Each of the half-shafts 72, 74 has an inner surface which defines a recess near the associated lip 61, 63 respectively. For example, the half-shaft 72 includes an inner surface 76 which defines a recess 81 near the lip 61. Similarly, the half-shaft 74 has an inner surface 78 which defines a recess 83 near the lip 63.

These recesses 81 and 83 are configured to receive a pair of blades 85, 87 respectively which are connected to the two electrical poles of the RF generator 47. Thus, the blade 85 is connected through a conductor 90 to the positive pole of the generator 47 while the blade 87 is connected through a conductor 92 to the negative pole of the generator 47. A layer of insulation 94 is sandwiched between the surfaces 76, 78 to separate the blades 85, 87. In this bipolar embodiment, current travels from the blade 85 through the tissue wall 18, around the insulation 94 and into the blade 87.

The exact configuration of the cutting elements 42, 85 and 87 in these embodiment is not important as long as the desired current density can be maintained. Thus the wire 42 and the blades 85 and 87 may be interchangable in the FIG. 1 and FIG. 2 embodiments.

Figure 5:
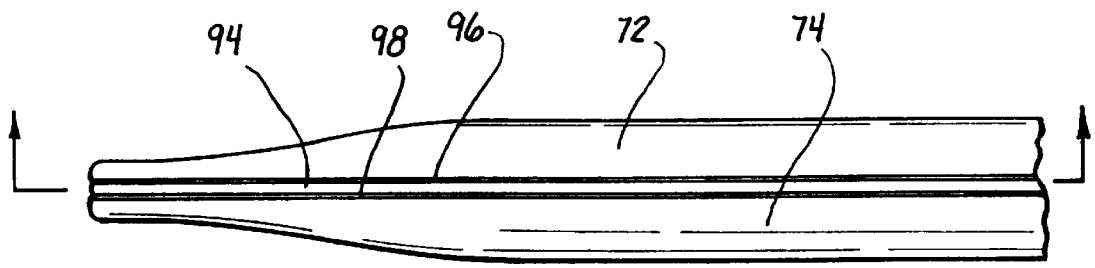
FIG. 5 is a side elevation view of a further embodiment of the trocar.
Figure 6:
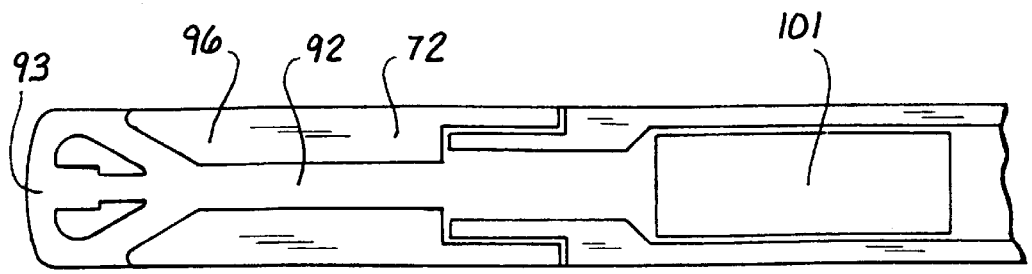
FIG. 6 is a cross-section view taken along lines 6—6 of FIG. 5.
Figure 7:
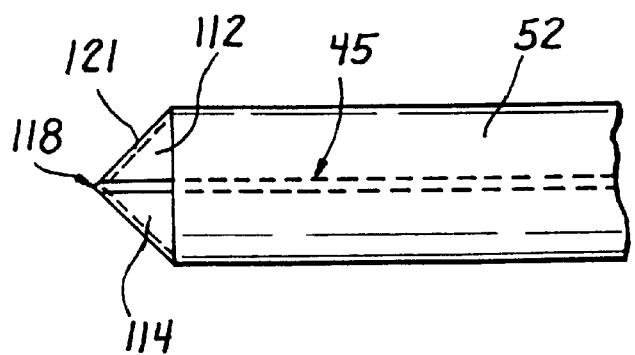
FIG. 7 is a side elevation view of a further embodiment of the trocar illustrating a plurality of wire cutting elements.
Figure 8:
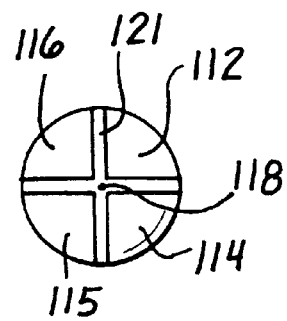
FIG. 8 is an end view of the embodiment illustrated in FIG. 7.

In a further embodiment of the invention illustrated in FIGS. 5 and 6, the shaft of the obturator 36 is again separated into the half-shafts 72 and 74. Along either or both of the interior surfaces 76, 78 a conducting material can be doped into or otherwise deposited on the material forming the half-shaft 72, 74. For example, in a preferred embodiment, the half-shafts 72, 74 are formed from glass or sintered ceramic and a pair of layers 96, 98 contain a conductive polymer or metal which is doped into the surfaces 76, 78 respectively. In a monopolar embodiment, only one of the layers 96, 98 is required. In the bipolar embodiment illustrated both layers 96, 98 are required as well as the insulation layer 94 which separates the two half-shafts 72, 74.

In this particular embodiment, the doped layer, for example the layer 98, can form both the cutting element, such as the blade 93, as well as the associated conductor, such as the conductor 92. The layer 98 may also include a region of epitaxial layering which forms a logic circuit 101 discussed in greater detail below.

Other embodiments of the invention which take advantage of the electrocautery technique are illustrated in FIGS. 7 through 11. In the FIG. 7 embodiment, which is also shown in the end view of FIG. 8, the distal end of the obturator 36 is formed with four planes or lands 112, 114, 115 and 116 which extend from the outer surface of the shaft 52 distally to a point 118. In this embodiment, a wire 121 is disposed along each of the lines defined by the intersection of the lands 112, 114, 115 and 116. In operation, the wires 121 cut the tissue of the wall 18 along four lines so that the incision is defined by four flaps of the tissue. This particular embodiment may be desirable where it is necessary to equalize pressures of the tissue on the outer surface of the cannula 32.

Figure 9:
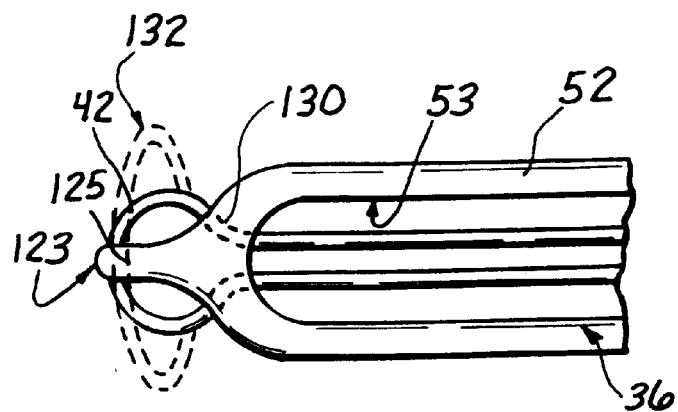
FIG. 9 is a side elevation view of still a further embodiment of the trocar with an expandable cutting element.

In the embodiment of FIG. 9, the distal end of the obturator 36 is formed with a projection 123 which extends distally and axially of the trocar 10. A recess or channel 125 is defined to extend generally radially across the projection 123. The cutting element or wire 42 in this embodiment passes down the axial channel 53 in the obturator 36 and passes outwardly of the shaft 52 through a port 127 at the distal end 12. The wire 42 then passes through the recess 125 in the projection 123 and back into the shaft 52 through a port 130.

This embodiment is of particular interest since either end of the wire 42 can be advanced distally within the axial channel 53 to expand the width of the wire 42 at the distal end of the trocar 10. In fact, both ends of the wire 42 can be moved distally to extend the exterior portions of the wire 42, for example to the dotted position 132 illustrated in FIG. 9. This position 132 has a significantly greater width and therefore provides a wider incision in the wall 18. Thus the wire 42 can be advanced and retracted within the axial channel 53 to vary the size and shape of the resulting incision.

Figure 10:
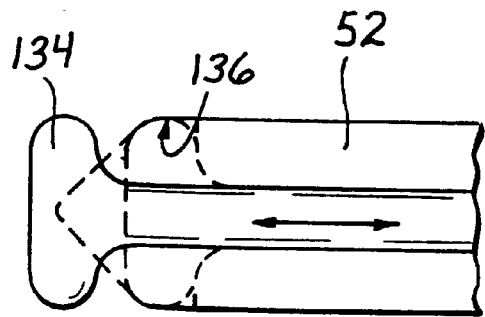
FIG. 10 is a top plan view of a further embodiment of a trocar with a retractable cutting element.
Figure 11:
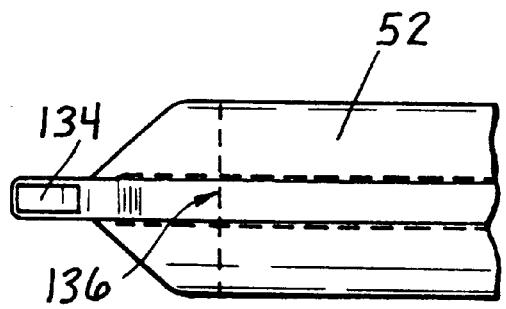
FIG. 11 is a side elevation view of the embodiment illustrated in FIG. 10.

In the embodiment of FIGS. 10, 11, the cutting element has the configuration of a blade 134 similar to that first discussed with reference to FIG. 3. In this case, the blade 134 can be advanced beyond the distal end of the shaft 52 associated with the obturator 36. It can also be retracted into a recess 136 in the shaft 52 in order to inhibit any further cutting of the tissue associated with the wall 18.

Figure 12:
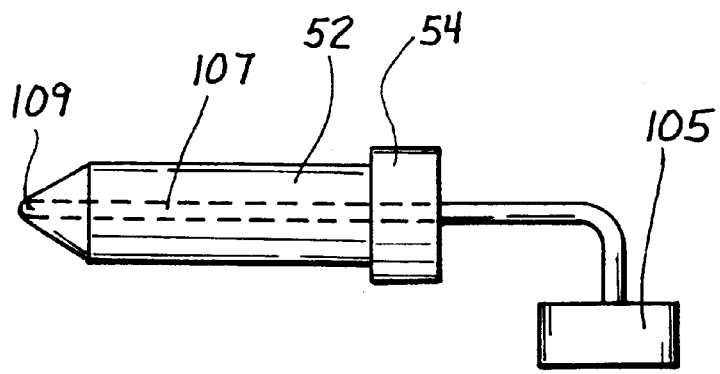
FIG. 12 is a schematic view of a trocar using an optical cutting system including a laser.

The invention is not limited to the electrocautery embodiments or techniques disclosed above. Rather, other types of cutting elements can be disposed at the distal end of the obturator 36 to increase the cutting capabilities of the trocar 10. One such embodiment is illustrated in FIG. 12 which provides for optical cutting in combination with a laser 105. The optical energy provided by the laser 105 is conducted through an optical fiber 107 to a cutting element or lens 109 which concentrates the energy to form the required incision in the wall 18.

It will be apparent to those skilled in the art that ultrasonic cutting is equally applicable to the present invention. In such a device, the conductor would transmit energy not in the radiofrequency range but rather in the ultrasonic range between 100 KHz and 1.2 MHz. As this energy emanates from the cutting element at the distal end of the trocar 10, the energy can be focused to activate the proximate cells and cause those cells to vaporize. Thus the ultrasonic cutter would function much as a microwave. One advantage of this system is that ultrasonic cutting does not require the two electrical poles associated with both monopolar and bipolar radiofrequency cutting. Focusing of the ultrasonic energy could be achieved with suitable wave guides.

One of the most significant problems confronting trocar procedures of the past has been associated with the need to compromise two conflicting requirements: 1) the requirement to provide a significant axial pressure to force the trocar 10 through the wall 18; and 2) the need to immediately cease application of that significant force upon penetration of the wall 18. Attempts have been made to address this problem automatically and mechanically with the provision of a protective sheath armed in a rearward position but biased to spring to a distal position covering the distal tip of the obturator 36 upon penetration of the wall 18.

This attempt to avoid relying totally on the surgeon for both of the conflicting requirements has met with only limited success. Since the protective sheath has necessarily been larger than the diameter of the obturator 36, the distal end 12 if the trocar has been required to move beyond the point of penetration in order to clear the distal end of the shield. In an attempt to provide reduced insertion forces, the angle between the axis 16 and the lands 112, 114, 115 and 116 has been reduced. While this has decreased the angle of inclination associated with these lands 112–116, it is also extended the length of the lands 112–116 rearwardly along the shaft 52. This has necessarily required that the protective sheath be thrown a greater distance in order to cover the point 118 of the obturator 36. The critical timing of this sheath response has not been sufficient to avoid the dramatic consequences associated with interior cutting.

Building on the advantages associated with the present invention whereby cutting by the obturator 36 is accomplished with electrical or optical energy, means can now be provided to sense complete penetration of the wall 18 and to cease further cutting by the cutting element.

Figure 13:
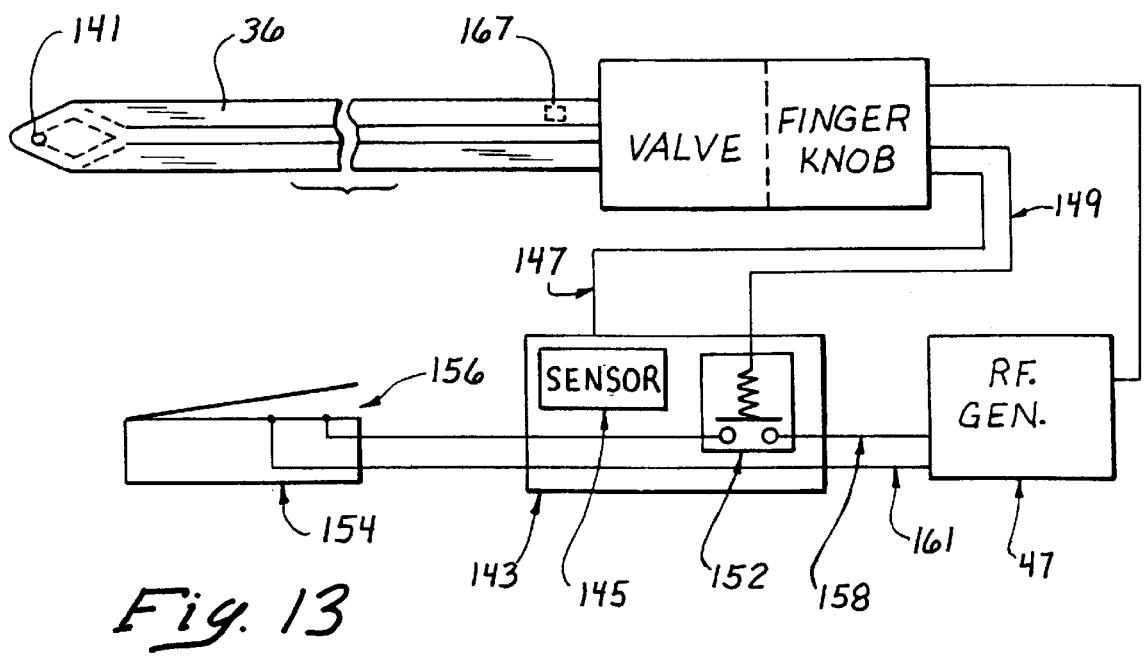
FIG. 13 is a schematic view of a preferred embodiment for sensing penetration of the tissue barrier.

With reference to FIG. 13, a particular embodiment of the obturator 36 may include means disposed near the distal end 12 of the trocar 10 for sensing penetration of the wall 18 by the obturator 36. The sensor 141 will typically be connected to a penetration detection and response circuit 143 which controls the RF generator through a pair of conductors 158, 161. In the illustrated embodiment, the circuit 143 includes an energy source 145 for energizing the sensor 141 through one or more conductors 147.

Upon penetration of the wall 18, the sensor 141 provides signal characteristics on a conductor 149. In a particular embodiment, a switch 152 can be included in the response circuit 143 and provided with characteristics responsive to the signal on the conductor 149 to deactivate the generator 47. Thus the switch 52 has characteristics for closing when the sensor 141 is in proximity to the tissue and for automatically opening when the sensor 141 detects penetration of the wall 18. This switch 152 can be interposed in series with a foot pedal 154 which includes a manual switch 156 for providing continuity between the two conductors 158, 161 which activate the generator 47.

Figure 14:
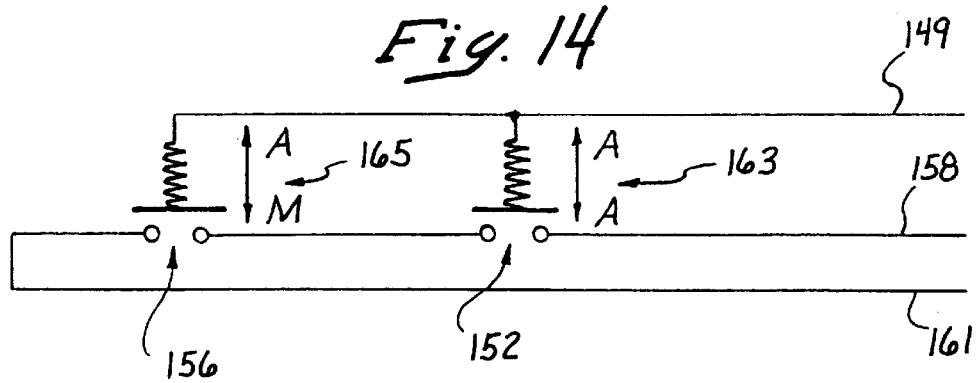
FIG. 14 is a schematic view of a switch system including an automatic switch and a manual override.

Under certain circumstances, it may be possible that the sensor 141 would detect the absence of pressure if the physician merely discontinues forward movement of the trocar 10 through the wall 18. Under these circumstances, a physician might decide to proceed with further cutting and therefore desire that the RF generator 47 be reactivated. This can be easily accomplished by the circuit 143 which is responsive to further pressure on the sensor 141 to close the switch 152. However, in a particular embodiment, it may be desirable to provide lock-out characteristics which require some manual switching, perhaps with a foot switch 156, in order to reactivate the generator 47. Such a circuit is illustrated schematically in FIG. 14 wherein the switches 152 and 156 are both responsive to the signal characteristics on conductor 149 to automatically open when the sensor 141 indicates that the wall 18 has been penetrated.

If additional pressure is detected by the sensor 141, the switch 152 would automatically close as illustrated by the Arrow 163. However, the switch 156 would require manual closure by the physician as illustrated by the arrow 165.

In other embodiments, the sensor 141 could be responsive to the presence or the pressure of insufflation gasses which are commonly used to inflate the abdominal cavity 27. These gases would be sensed only on the interior side of the wall 18 so the sensor 141 would actually be detecting penetration of the wall 18 by the obturator 36. These gas pressures could also be sensed in an embodiment providing for a longitudinal channel, such as the axial channel 53, which could convey the pressures to the sensor 141 at a more proximal location such as that illustrated at the dotted position 167 in FIG. 13.

Figure 15:
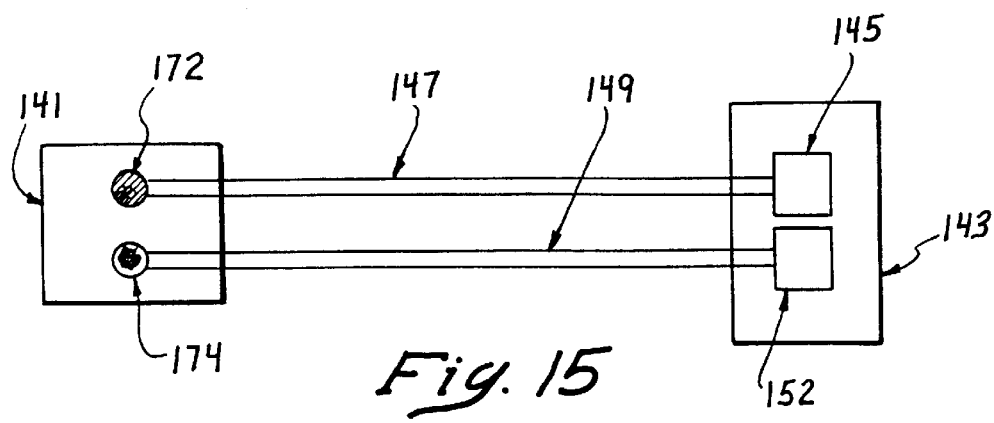
FIG. 15 is a schematic view of a infrared system for detecting penetration of the tissue barrier.

In still a further embodiment, the sensor 141 could be an infrared sensor including an LED 172 activated by the energizer 145 and a detector 174 providing the switch 152 with signal characteristics on the conductor 149. Such an IR sensor 141 as illustrated in FIG. 15 would sense the proximity of tissue by the reflectance of light from the LED 172 to the detector 174.

Another way of sensing penetration of the wall 18 is particularly adapted for the embodiment illustrated in FIGS. 5 and 6. In this case, the logic circuit 101 provides means for sensing changing electrical characteristics in proximity to the cutting element, such as the blade 93. These electrical characteristics may include capacitance, resistance, current magnitude, current density, or any combination thereof. These characteristics will tend to vary most dramatically as the blade 93 approaches the interior surface of the wall 18. As the tissue surrounding the blade 92 is reduced in thickness, the resistance to current flow will rise. Not only will the magnitude of the current in conductor 92 decrease, but the density of the current passing through the tissue will also tend to decrease. Any one or all of these characteristics can be detected by the logic circuit 101 to provide a means for inhibiting further cutting of tissue upon complete penetration of the wall 18.

Although this invention has been discussed with reference to various electrical and optical cutting circuits and exemplary switching circuits, it will be apparent to those skilled in the art that the invention can be otherwise embodied. Generally, any energy source can be coupled to the distal end of the obturator 36 and its energy converted into forms suitable for cutting tissue. Various cutting elements and cutting element configurations will be apparent depending on the nature of the energy provided. Various types of technology can also be incorporated into the sensor 141 all with the intent to provide some measurable indication at the point in time when the obturator 36 penetrates the wall 18.

Due to the broad nature of this invention, the breadth of the associated concept should not be limited merely to the disclosed embodiments or the drawings, but should be determined only with reference to the following claims.

We claim:

1. An obturator for creating an incision through a tissue barrier, including:
   a rod having a longitudinal axis and an outer surface which converges toward a distal tip;
   portions of the rod defining a slot extending transverse to the axis at the distal tip of the rod;
   means disposed in the slot for conducting energy to the distal tip of the rod; and means for energizing the conducting means to cut the tissue when the distal tip of the rod is moved into proximity with the tissue and when the rod is advanced through the tissue to create the incision.

2. The obturator recited in claim 1 further comprising:
means for sensing penetration of the tissue barrier by the distal tip of the rod; and
means for inhibiting the energizing means when penetration is sensed by the sensing means.

3. The obturator recited in claim 2 wherein the inhibiting means includes a switch disposed along the conducting means and being responsive to the sensing means to inhibit conduction of the energy to the distal tip of the rod, whereby cutting of the tissue ceases upon penetration of the tissue barrier.

4. The obturator recited in claim 1 wherein the portions of the rod comprise a pair of lips defining the slot at the distal tip of the rod, the lips extending distally of the energy conducting means in the slot.

5. The obturator recited in claim 4 wherein:
the energy conducting means comprises a wire having a diameter and extending through the slot transverse to the axis of the rod; and
the lips extend distally a distance greater than the diameter of the wire.

6. The obturator recited in claim 1 wherein the rod is formed of insulative materials having properties non-conductive of the energy.

7. A surgical trocar assembly for penetrating a barrier of tissue and for providing an operative channel through the tissue barrier and into a body cavity, including:
an operative sleeve having a distal end and being adapted for disposition across the tissue barrier with the distal end of the sleeve located in the body cavity, the sleeve defining the operative channel with a size sufficient to receive surgical instruments for performing surgery within the body cavity;
an obturator removably disposed in the sleeve and including an axis and a distal end extending beyond the distal end of the sleeve;
a source of energy;
a cutting element disposed at the distal end of the obturator and adapted to be moved axially into contact with the tissue and to be moved axially through the tissue barrier out of contact with the tissue;
means for conducting the energy from the source to the cutting element and for energizing the cutting element to cut the tissue;
at least one conductor included in the conducting means and disposed along a conduction path extending from the source of energy to the distal end of the obturator assembly;
switch means included in the conducting means and disposed in the conductive path for permitting the conduction of energy to the cutting element in a first state and for inhibiting the conduction of energy to the cutting element in a second state;
means responsive to the cutting element being out of contact with the tissue for placing the switch means in the second state; and
whereby the distal end of the obturator and the distal end of the sleeve can be advanced through the cut tissue to penetrate the tissue barrier, and the obturator can be removed from the sleeve leaving the sleeve operatively disposed across the tissue barrier with the channel appropriately sized to receive the surgical instruments.

8. The surgical trocar assembly recited in claim 7 wherein the source of energy is a laser.

9. The surgical trocar assembly recited in claim 7 wherein the cutting element is a bi-polar radio frequency electrode including a first electrode, a second electrode and insulation means disposed between the first electrode and the second electrode.

10. A method for inserting a cannula through the wall of a body cavity, comprising the steps of:
inserting an energy conductive cutting device through the cannula, the device being longitudinal in configuration with a cutting element disposed at a distal tip of the device;
contacting the wall of the cavity with the energy conductive cutting element of the device;
energizing the conductive cutting element at the distal tip of the device to cut the wall of the cavity;
during the energizing step advancing the tip of the device distally to create a hole through the wall of the cavity; and
during the advancing step, maintaining a substantially constant area of contact between the cutting element and the wall of the cavity.

11. The method recited in claim 10 further comprising the step of de-energizing the cutting element when the distal end of the device penetrates the wall of the cavity.

12. The method recited in claim 11 further comprising the step of providing the cutting element with at least one pole of an electrosurgical cutter.

13. The method recited in claim 12 wherein the providing step includes the step of providing the energy conductive cutting element with at least one electrosurgical wire.

14. The method recited in claim 11 further comprising the step of providing the energy conductive cutting element with a blade.

15. A surgical apparatus for creating an incision through a tissue barrier, including;
a rod having walls disposed along a longitudinal axis, the walls converging generally toward a line extending transverse to the axis at the distal end of the rod, portions of the walls defining a pair of opposing lips which extend laterally of the rod at the distal end of the rod;
means disposed at the distal end of the rod and extending at least a portion of the distance along the line for conducting energy at the distal tip to cut the tissue barrier, the lips defining a slot extending transverse to the axis of the rod and being configured to receive the energy conducting means; and
means for energizing the conducting means to cut the tissue when the rod is placed in proximity to the tissue and when the rod is moved axially through the tissue to create the incision.

16. The apparatus recited in claim 15 wherein the line has a length which extends generally perpendicular to the axis of the rod.

17. The apparatus recited in claim 16 wherein the energy conducting means is disposed across the entire length of the line.

18. The apparatus recited in claim 15 wherein the slot has an axial dimension and the energy conducting means comprises a wire having a length extending along the slot and a diameter which is less than the axial dimension of the slot.

19. A trocar system for creating an incision through the body tissue, including:
a cannula forming a channel adapted to receive surgical instruments;

an obturator sized and configured to extend through the instrument channel of the cannula, the obturator having a longitudinal axis and a cross-sectional dimension which narrows to form a tip at a distal end of the obturator;

the distal tip of the obturator being defined by at least one ramp which has an angular relationship with the axis of the obturator, and which extends into proximity with a line extending transverse to the axis generally at the distal end of the obturator;

means disposed along the line for conducting energy at the distal end of the obturator; and means for energizing the conducting means to cut the tissue when the obturator is placed in close proximity to the tissue and when the obturator is moved through the tissue to create the incision.

20. The trocar system recited in claim 19 wherein the ramp has a generally planar surface.

21. The trocar system recited in claim 20, wherein:

the ramp comprises a first ramp having a first generally planar surface extending distally to a first lip; the obturator further comprises a second ramp having a second generally planar surface extending distally to a second lip; and the line extends between the first lip and the second lip and generally parallel to the first lip and second lip.

22. The trocar system recited in claim 21 wherein:

the second surface is a generally planar surface and has an angular relationship with the axis of the obturator; and the line is a straight line.

23. A trocar system for creating an incision in tissue including:

a cannula forming a channel adapted to receive surgical instruments;

an obturator sized and configured for removable disposition in the instrument channel of the cannula, the obturator having a longitudinal axis extending between a proximal end and an opposing distal end of the obturator;

a conductor disposed at the distal end of the obturator and having a side surface with a length and a width, the side surface being oriented to face distally outwardly of the obturator with its length disposed generally transverse to the axis of the obturator; and means for energizing the conductor at the distal end of the obturator to cut the tissue and create the incision when the obturator is placed in proximity to the tissue.

24. The trocar system recited in claim 23 wherein the conductor comprises at least one pole of an electrosurgical instrument.

25. The trocar system recited in claim 24 wherein the conductor comprises one pole of a bi-polar electrosurgical instrument.

26. The trocar system recited in claim 23 wherein the conductor has a longitudinal configuration and extends laterally of the obturator and transverse to the axis at the distal tip of the obturator.

27. The trocar system recited in claim 26 wherein:

the obturator in axial cross-section has a maximum width; and the length of the surface of the conductor is at least as long as the maximum width of the obturator.

28. A method for providing a working channel across a body wall defining a cavity, the channel being of a size sufficient to receive instruments adapted to perform surgery within the cavity, comprising the steps of:

providing a sleeve having walls which define the working channel and extend to a distal end of the sleeve;

providing an obturator having an energy conductive element disposed at a distal tip of the obturator;

during the second providing step, providing an obturator shaft having an axis and an outer surface which converge at the distal tip;

during the second providing step, positioning the energy conductive element to extend transverse to the axis at the distal tip of the obturator shaft;

inserting the obturator into the working channel of the sleeve with the distal tip of the obturator extending beyond the distal end of the sleeve;

moving the obturator and the sleeve into proximity with the body wall;

electrically energizing the conductive element at the distal tip to create an incision in the body wall;

advancing the obturator and the sleeve through the incision until the distal end of the sleeve is positioned in the cavity;

removing the obturator from the sleeve to open the working channel into the cavity; and inserting the instruments into the working channel of the sleeve to perform surgery within the cavity.

29. The method recited in claim 28 wherein:

the step of providing the obturator further comprises the step of providing the energy conductive element in the form of a wire; and the penetrating step includes the step of positioning the wire to extend generally perpendicular to the axis of the obturator shaft.

* * * * *